(12) United States Patent
Dittmar et al.

(10) Patent No.: US 9,849,263 B2
(45) Date of Patent: Dec. 26, 2017

(54) METHOD AND DEVICE FOR SUPPLYING OXYGEN TO A PATIENT

(71) Applicant: Touchfree O2 LLC, Richland, WA (US)

(72) Inventors: Edbert E. L. Dittmar, Coeur d'Alene, ID (US); Sidney Smith Rodabough, Richland, WA (US); Kenneth Elwin Kenyon, Issaquah, WA (US)

(73) Assignee: Touchfree O2 LLC, Richland, WA (US)

( * ) Notice: Subject to any disclaimer, the term of this patent is extended or adjusted under 35 U.S.C. 154(b) by 294 days.

(21) Appl. No.: 14/206,745

(22) Filed: Mar. 12, 2014

(65) Prior Publication Data
US 2014/0311485 A1    Oct. 23, 2014

Related U.S. Application Data

(60) Provisional application No. 61/777,663, filed on Mar. 12, 2013.

(51) Int. Cl.
*A61M 16/10* (2006.01)
*A61H 33/00* (2006.01)
(Continued)

(52) U.S. Cl.
CPC ......... *A61M 16/1005* (2014.02); *A61H 33/60* (2013.01); *A61M 16/12* (2013.01);
(Continued)

(58) Field of Classification Search
CPC ....... A61H 33/14; A61M 16/00; A61M 16/06; A61M 16/104
See application file for complete search history.

(56) References Cited

U.S. PATENT DOCUMENTS 2,628,803 A * 2/1953 Krewson ............... A61M 16/06
                                                  128/200.24
3,683,907 A    8/1972 Cotabish
(Continued)

OTHER PUBLICATIONS

Davies et al, "The Efficacy of Noncontact Oxygen Delivery Methods", Pediatrics, Nov. 2002, pp. 964-967, vol. 110, No. 5, pediatrics.aappublications.org.
(Continued)

*Primary Examiner* — Justine Yu
*Assistant Examiner* — Kathrynn Lyddane
(74) *Attorney, Agent, or Firm* — Thorpe North & Western LLP (57) ABSTRACT

A system for delivering oxygen to a substantially stationary patient without coupling a device to the body of the patient is disclosed. The system includes a source of oxygen coupled to a delivery system wherein the delivery system has a pump configured to pressurize oxygen and an elongate hollow member operatively coupled to the pump. The elongate hollow member has a proximal end and a distal end and is constructed to receive oxygen in its proximal end and deliver oxygen to the patient out the distal end. The length and diameter of the elongate member, the flow of oxygen through the elongate member, and the distance from the distal end of the elongate member to the face of the patient are optimized to collimate a stream of oxygen such that when the stream of oxygen reaches the patients face it envelops the face of the patient.

17 Claims, 4 Drawing Sheets

(51) Int. Cl.
*A61M 16/12* (2006.01)
*A61H 33/14* (2006.01)

(52) U.S. Cl.
CPC ..... *A61H 2033/143* (2013.01); *A61M 16/125* (2014.02); *A61M 2202/0208* (2013.01); *A61M 2209/082* (2013.01)

(56) References Cited

U.S. PATENT DOCUMENTS

| | | | | |
|---|---|---|---|---|
| 4,282,869 | A | * | 8/1981 | Zidulka ............. A61M 16/0683 128/200.28 |
| 4,321,917 | A | * | 3/1982 | Campbell ................ A61G 7/05 128/200.24 |
| 4,444,183 | A | * | 4/1984 | Heckendorn ..... A61M 16/0627 128/204.18 |
| 5,389,037 | A | * | 2/1995 | Hale ....................... F24F 7/065 128/204.18 |
| 5,690,096 | A | * | 11/1997 | Burch ................... A61M 16/06 128/200.24 |
| 6,065,473 | A | | 5/2000 | McCombs et al. |
| 6,247,470 | B1 | | 6/2001 | Ketchedjian |
| 6,631,719 | B2 | | 10/2003 | McDonald et al. |
| 6,910,961 | B2 | * | 6/2005 | Niu ........................ B60H 1/246 454/333 |
| D515,697 | S | | 2/2006 | Nakamura et al. |
| 7,036,502 | B2 | | 5/2006 | Manne |
| 7,694,680 | B2 | | 4/2010 | Brichetto |
| 9,180,262 | B2 | * | 11/2015 | Cota ...................... A61M 11/06 |
| 2009/0236004 | A1 | * | 9/2009 | Jani ........................ F16L 11/083 138/127 |
| 2011/0004151 | A1 | * | 1/2011 | Simonsen ............. A61M 35/00 604/23 |
| 2012/0240930 | A1 | * | 9/2012 | Kristensson ........... A61G 10/02 128/204.16 |

OTHER PUBLICATIONS

Hanson et al, "Optimizing a Non-Contact Pediatric Oxygen Delivery System", ME 4054—Design Projects University of Minnesota, May 2010, 30 pages, designwise medical.

Shih et al, "The Efficacy of Oxygen Wafting Using Different Delivery Devices, Flow Rates, and Device Positioning", SAEM Annual Meeting Abstracts, 2011, p. S8.

* cited by examiner

METHOD AND DEVICE FOR SUPPLYING OXYGEN TO A PATIENT

PRIORITY CLAIM

This application claims priority to U.S. Provisional Application No. 61/777,663 filed on Mar. 12, 2013 entitled "Method and Device for Supplying Oxygen to a Patient" which is incorporated herein by reference in its entirety.

FIELD OF THE TECHNOLOGY

The present technology relates to devices for delivery of oxygen to a patient and more particularly to delivery mechanisms intended to deliver oxygen to a patient without the need for a mask or cannula attached to the face of the patient.

BACKGROUND OF THE TECHNOLOGY AND RELATED ART

Oxygen therapy is the administration of oxygen as a medical intervention, which can be for a variety of purposes in both chronic and acute patient care. Oxygen is essential for cell metabolism, and in turn, tissue oxygenation is essential for all normal physiological functions. High blood and tissue levels of oxygen can be helpful or damaging, depending on circumstances, and oxygen therapy should be used to benefit the patient by increasing the supply of oxygen to the lungs and thereby increasing the availability of oxygen to the body tissues, especially when the patient is suffering from hypoxia and/or hypoxemia.

A common use of supplementary oxygen is in patients with chronic obstructive pulmonary disease (COPD), the occurrence of chronic bronchitis or emphysema or others who may require additional oxygen to breathe either during a temporary medical condition, or a chronic lack of oxygen absorption. Oxygen is sometimes prescribed for people with breathlessness, in the setting of end-stage cardiac or respiratory failure, or advanced cancer or neurodegenerative disease despite having relatively normal blood oxygen levels. Various devices are used for administration of oxygen. In many cases, the oxygen will first pass through a pressure regulator, used to control the high pressure of oxygen delivered from a cylinder (or other source) to a lower pressure. This lower pressure is then controlled by a flow meter, which may be preset or selectable which controls the flow in a measure such as liters per minute (LPM). A typical flow meter range for medical oxygen is between 0 and 15 LPM though some units may be able to produce up to 25 LPM.

Many patients require only a supplementary level of oxygen in the room air they are breathing, rather than pure or near pure oxygen which can be delivered through a number of devices dependent on the situation, the required flow rate of oxygen and, in some instances, patient preference. For example, a nasal cannula is a thin tube with two small nozzles that protrude into the patient's nostrils. It can only comfortably provide oxygen at low flow rates (approximately 2 to 6 LPM) delivering an air stream with an oxygen concentration of 24 to 40 percent.

While there are many concerns that have been raised by medical practitioners regarding the use of oxygen therapy and supplemental oxygen supply to patients (e.g., aspiration of vomitus, etc.), for purposes of the present application, patients are known to suffer significant discomfort and inconvenience as a result of the use of oxygen masks or nasal cannula. Extended use of said devices irritates the skin of patients often resulting in secondary trauma to areas where the devices come into contact with the patient (e.g., ears, nose, and sides of face). Additionally, face masks and nasal cannula restrict the movement of the patient. This may cause the patient to suffer from stiffness due to decreased range of motion of the body and have a negative impact on the patient's ability to sleep. This is particularly true for a patient whose sleep patterns involve regular movement during the course of sleep who can often wake to find the nasal cannula removed from the nose and/or tangled about the body. Other patients that suffer from dementia or claustrophobia, for example, simply refuse to wear a face mask or nasal cannula.

Prior art devices have sought to solve some of the identified deficiencies by creating a headband and tubular boom directing air to the face of the patient without having to have a mask or nasal cannula. This approach, however, still requires that the patient wear a head band that can irritate the skin over time and also limit range of motion and disturb sleep. Others have sought to resolve the irritation associated with extensive wearing of devices with non-petroleum lubricants on the face and nose or foam guards to protect the ear, for example. Numerous other similar prior art devices attempt to solve the above-referenced problems in a similar manner but without an effective solution. Due to the problems and inefficiencies associated with prior art oxygen delivery systems, a need exists for improved systems and methods of oxygen delivery to patients that will minimize patient discomfort.

BRIEF DESCRIPTION OF THE DRAWINGS

The present technology will become more fully apparent from the following description and appended claims, taken in conjunction with the accompanying drawings. Understanding that these drawings merely depict exemplary aspects of the present technology they are, therefore, not to be considered limiting of its scope. It will be readily appreciated that the components of the present technology, as generally described and illustrated in the figures herein, could be arranged and designed in a wide variety of different configurations. Nonetheless, the technology will be described and explained with additional specificity and detail through the use of the accompanying drawings in which:

DETAILED DESCRIPTION OF EXEMPLARY ASPECTS

The following detailed description of exemplary aspects of the technology makes reference to the accompanying drawings, which form a part hereof and in which are shown, by way of illustration, exemplary aspects in which the technology may be practiced. While these exemplary aspects are described in sufficient detail to enable those skilled in the art to practice the technology, it should be understood that other aspects may be realized and that various changes to the technology may be made without departing from the spirit and scope of the present technology. Thus, the following more detailed description of the aspects of the present technology is not intended to limit the scope of the technology, as claimed, but is presented for purposes of illustration only and not limitation to describe the features and characteristics of the present technology, to set forth the best mode of operation of the technology, and to sufficiently enable one skilled in the art to practice the technology. Accordingly, the scope of the present technology is to be defined solely by the appended claims.

The following detailed description and exemplary aspects of the technology will be best understood by reference to the accompanying drawings, wherein the elements and features of the technology are designated by numerals throughout. The present technology describes a system and method for efficiently delivering oxygen to the face of a patient without the need for a device worn on the patient's face. Patients are prescribed a dose of oxygen the medical personnel determine is required for patient treatment and/or care. Delivery of a proper dose of oxygen is therefore important.

It is intended that the system of the present technology be operable with different types of functional attachments or components so long as the end result is delivery of a quantity of oxygen to a substantially stationary (i.e., sleeping, laying, sitting, etc.) patient sufficient to meet the patient's needs. Bearing that in mind, the oxygen delivery system of the present technology, in accordance with one aspect of the technology, may be broadly described as a source of oxygen coupled to a delivery system, the system comprising a pump configured to pressurize oxygen emanating from the source of oxygen and an elongate hollow member having a proximal end and a distal end, configured to receive pressurized oxygen in its proximal end and deliver oxygen to the patient out the distal end. The length and diameter of the elongate member, the flow of oxygen through the elongate member, the distance from the distal end of the elongate member to the face of the patient, and the angle of the elongate member with respect to the face of the patient are optimized to collimate a stream of oxygen such that when the stream of oxygen comes in contact with the face of the patient, it envelops the face of the patient and delivers a prescribed dose of oxygen to the patient. As used herein, the terms "stream of oxygen," "oxygen flow," and the like refer generally to an oxygen-enriched stream of air. The oxygen concentration within that stream of air is generally greater than ninety percent.

Generally speaking, in fluid dynamics, turbulence or turbulent flow is a flow regime characterized by chaotic and stochastic property changes. This includes low momentum diffusion, high momentum convection, and rapid variation of pressure and velocity in space and time. Usually characterized by high levels of kinetic energy, turbulent flows are always highly irregular. The readily available supply of energy tends to accelerate the homogenization (mixing) of fluid mixtures. The characteristic which is responsible for the enhanced mixing and increased rates of mass, momentum and energy transports in a flow is called "diffusivity." To sustain turbulent flow, a persistent source of energy supply is required because turbulence dissipates rapidly as the kinetic energy is converted into internal energy by viscous shear stress. Part of the dissipation of this energy results in the formation of eddies of many different length scales. Most of the kinetic energy of the turbulent motion is contained in the large-scale structures. The energy "cascades" from these large-scale structures to smaller scale structures by an inertial and essentially inviscid mechanism. This process continues creating smaller and smaller structures which produces a hierarchy of eddies. Eventually this process creates structures that are small enough that dissipation of energy finally takes place. This process is exacerbated by the exit-opening or orifice associated with the production of a fluid stream. The boundaries about the external fluid stream are in contact with an opening edge or orifice edge that further contributes to turbulent flow and the creation of eddies.

In one aspect of the technology, a length of tubing is coupled to an oxygen source and disposed about the face of a patient. Oxygen (i.e., an oxygen-enriched stream of air) is then directed to the patient through the tubing. If the tubing is placed too close to the patient, however, patient movement and comfort is limited. If the tubing is placed too far from the patient, the stream of oxygen is mixed with ambient air due to a turbulent air flow before reaching the patient. This results in unacceptable dilution of the dose of oxygen to be consumed by the patient. An unchecked increase in the velocity of the oxygen stream does not solve this problem due to the increase in turbulence resulting from the increase in velocity. An unchecked increase in oxygen results in unwanted fire hazards and an unnecessary increase in costs.

Figure 1:
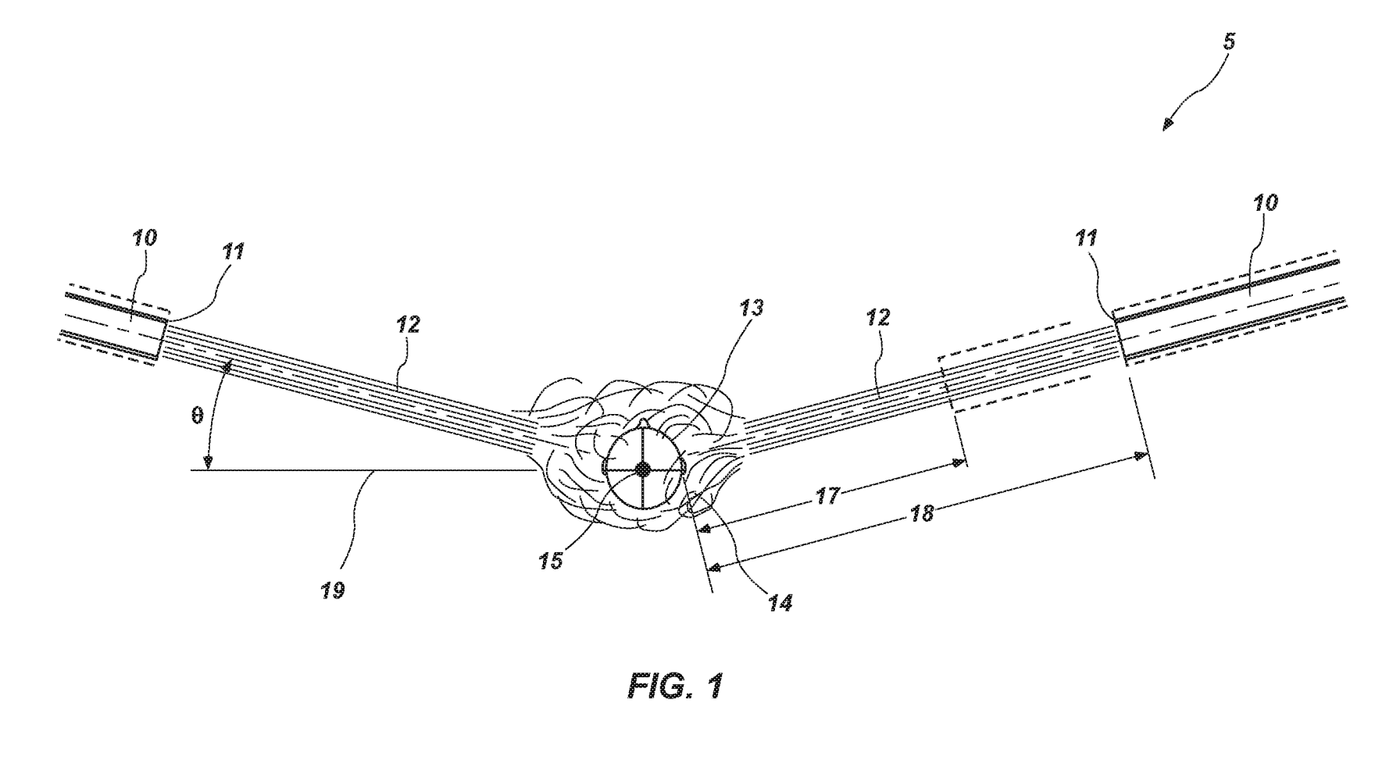
FIG. 1 is a diagram illustrating an oxygen delivery system in accordance with one aspect of the technology.

With specific reference to FIG. 1, in accordance with one aspect of the technology, an oxygen delivery system 5 comprising a length of tubing 10 is disclosed. The length of tubing (or elongate hollow member) 10 comprises medical-grade metals, silicone, poly-vinyl chloride, polyethylene, polyurethane, or other composite material coupled to a pressurized source of oxygen and a flow meter for regulating the volume of oxygen flow from the oxygen source (i.e., an oxygen concentrator). In one aspect of the technology, tubing is chosen to minimize frictional losses (i.e., having a low coefficient of friction) within the tube thus maximizing the energy of the fluid stream as it passes through the tubing and minimizing turbulence as the fluid stream exits the tubing. The length and diameter of the tubing 10 are configured to optimize collimation of the fluid stream as it exits the distal end 11 of the tubing 10. Advantageously, by optimizing collimation of the fluid stream, diffusion or mixing of the oxygen stream with ambient air is minimized. In this manner, a distal end 11 of the tubing 10 is optimally placed a predetermined distance from the face of the patient 13 such that the collimated stream of oxygen 12 exits the tube 10 in a substantially laminar state. The stream 12 maintains a laminar state until it nears the face of the patient 13 where it transforms from a laminar state to a turbulent state. Advantageously, optimizing the location of the transformation of the oxygen stream 12 from a laminar to a turbulent state with respect to the face of the patient 13 results in an oxygen cloud 14 enveloping the patient's face. In this manner, the dose of oxygen prescribed by medical personnel is efficiently and effectively delivered to the patient for consumption without the need for a face mask or nasal cannula.

Figure 2:
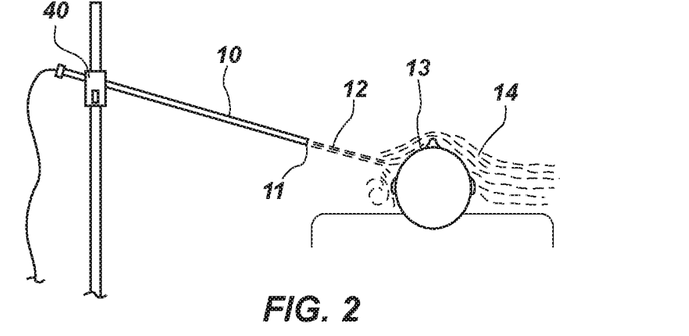
FIG. 2 is an oxygen delivery system in accordance with one aspect of the technology with the head of the patient in a first position.
Figure 3:
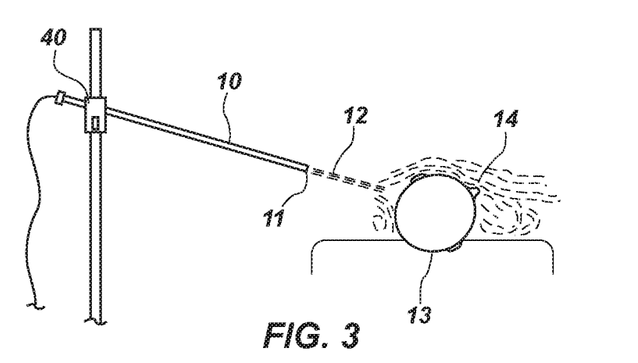
FIG. 3 is an oxygen delivery system in accordance with one aspect of the technology with the head of the patient in a second position.
Figure 4:
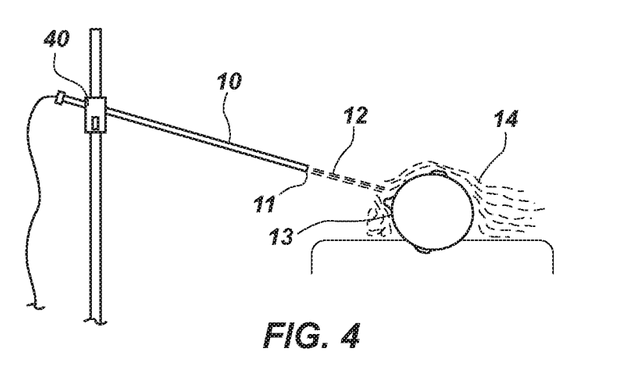
FIG. 4 is an oxygen delivery system in accordance with one aspect of the technology with the head of the patient in a third position.
Figure 5:
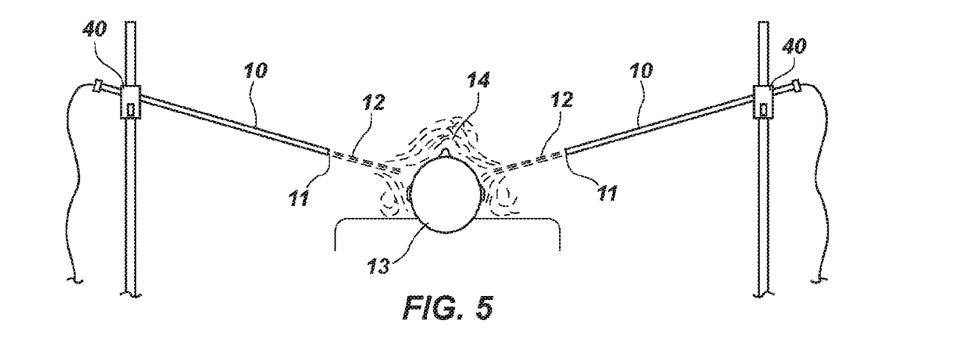
FIG. 5 is an oxygen delivery system in accordance with one aspect of the technology with the head of the patient in a first position.
Figure 6:
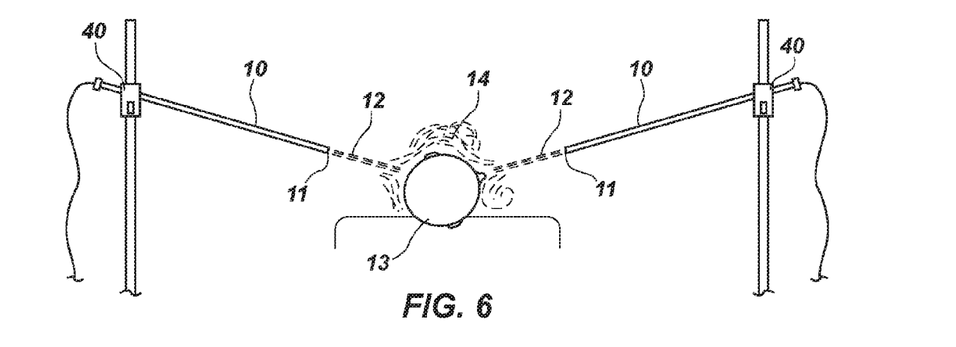
FIG. 6 is an oxygen delivery system in accordance with one aspect of the technology with the head of the patient in a second position.
Figure 7:
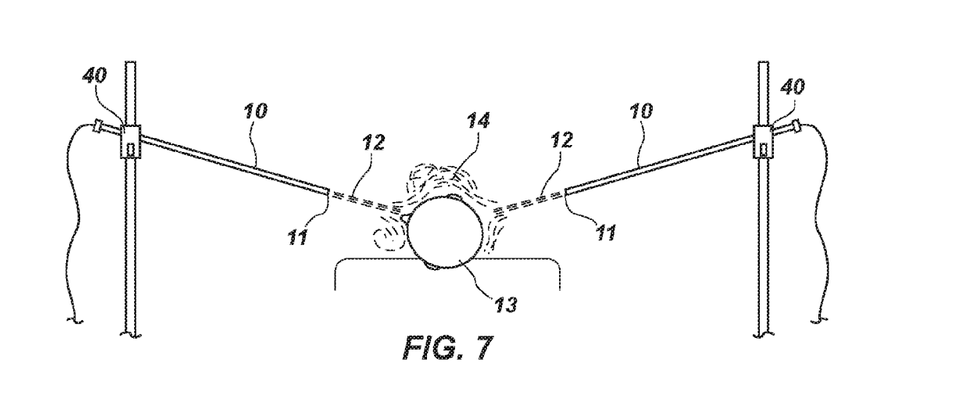
FIG. 7 is an oxygen delivery system in accordance with one aspect of the technology with the head of the patient in a third position.

FIGS. 1 and 5 through 6 show one aspect of the technology having two streams. With reference to FIGS. 2 through 4, an aspect of the technology with one stream is shown. It is believed that the oxygen cloud 14 is dynamic. That is, when the oxygen stream 12 is directed to one side of the face of the patient 13, the turbulent cloud 14 moves from one side of the face to the other side of the face due to the frictional forces encountered on the face of the patient 13 and the resulting pressure gradient induced by the change in velocity of the fluid stream 12. Advantageously, it is believed that the resulting oxygen cloud 14 delivers a dose of oxygen to the patient 13 regardless of the direction of his or her face. In other words, the patient 13 may be sleeping with his or her face positioned opposite to the direction of flow emanating from the tubing 10. However, due to the movement of the oxygen cloud 14 about the face of the patient 13, an effective dose of oxygen is still delivered to the patient 13.

With reference generally to FIGS. 1 through 7, the inner diameter of the tubing 10 ranges from approximately 5 to 16 millimeters. Depending on the desired oxygen delivery rate, a substantially straight length of the tubing 10 required to effectively collimate the oxygen stream 12 ranges from approximately 300 mm to 1000 mm with a preferred length being longer for larger diameter tubes. In other words, while the tubing 10 that is used to couple the system 5 generally to an oxygen source may be of any suitable length, the section of tubing 10 that is longitudinally directed towards the head of the patient 13 and which functions to collimate the oxygen stream 12 is substantially straight and ranges from approximately 300 mm to 1000 mm. In order for the collimating function to efficiently take place, no substantial bends or occlusions to the oxygen stream 12 within the tubing 10 should occur along the 300 mm to 1000 mm length of tubing.

The flow rate of the oxygen stream 12 ranges from approximately 4 to 12 liters per minute (LPM) with the actual flow rate determined by the prescriber ordering the blood oxygen saturation rate. The distance from the distal end 11 of tubing 10 to the head of the patient 13 ranges from approximately 150 mm (shown at 17) to 300 mm (shown at 18) with a preferred minimum distance of 180 mm. In accordance with one aspect of the technology, the tubing 10 is arranged at an angle ⊖ with respect to an imaginary longitudinal plane 19 collinear with the centroid 15 and the top of the head of the patient 13. That angle ranges from approximate zero to forty-five degrees. In one aspect of the technology, the tubing 10 is disposed at an angle of fifteen degrees from the imaginary longitudinal plane 19 and is directed to the mouth and nose or slightly below the mouth of 25 the patient 13.

In accordance with one aspect of the technology, an oxygen delivery system 5 comprising two tubes is contemplated for use. In one aspect, the two tubes are diametrically opposed about the centroid 15 of the head of the patient 13. Two oxygen streams 12 and the resulting oxygen cloud 14 provides additional assurance that the patient 13 is receiving the prescribed dose of oxygen. In this aspect of the technology, the flow rate from each of the opposing tubes is approximately equal. A calculated preferred flow rate (e.g., 10 LPM) is equally divided between the two tubes (e.g., by a "Y" connector) so that a substantially equal amount of oxygen is delivered to either side of the patient 13. In other words, the prescribed oxygen dose is divided between the two tubes, one tube delivering half of the oxygen dose while the other tube concurrently delivers the other half of the dose.

In accordance with one aspect of the technology, a laser guide is mounted on the tubing 10. The laser guide is arranged so that the direction of the laser is parallel to the direction of the oxygen stream 12 having a center within a few millimeters of the center of the oxygen stream 12. Another method of aligning the tubes 10 is by projecting a light directly through the tube 10 and onto the patient's face. In this manner, medical personnel can properly point the tubing 10 to the appropriate portion of the face of the patient 13, regularly check on the arrangement of the tubing 10 with respect to the patient 13, and make any necessary adjustments to the tubing 10. In another aspect of the technology, the distal end 11 of the tubing 10 may be disguised as a common household or hospital room item to prevent patients with dementia or Alzheimer's from disturbing the tubing arrangement. Moreover, the distal end 11 of the tubing 10 may comprise a ball or other non-blunt surface to minimize risks associated with patient collision with the distal end 11 of the tubing 10.

In accordance with one aspect of the technology, a method of providing oxygen to a patient without a mask or nasal cannula is disclosed. The method comprises connecting an elongate hollow tube to a source of oxygen and means (e.g., a pump) for pressurizing oxygen for delivery to a patient via the tube. The length and diameter of the elongate member, the flow of oxygen through the elongate member, and the distance from the distal end of the elongate member to the face of the patient are optimized to collimate a stream of oxygen such that when the stream of oxygen comes in contact with the face of the patient it envelops the face of the patient. It is further configured to maintain a laminar oxygen stream until it nears the face of the patient where it is transformed to a turbulent state. The table below provides example dimensions of some of these optimized parameters.

| Flow Rate (LPM) | Tube Cross Section Area (cm$^2$) | Inside Tube Diameter (mm) | Inside Tube Diameter for Two-Tube System (mm) |
| --- | --- | --- | --- |
| 10 | 1.67 | 14.6 | 10.3 |
| 8 | 1.33 | 13 | 9.2 |
| 6 | 1.00 | 11.3 | 8 |
| 4 | 0.67 | 9.2 | 6.5 |
| 2 | 0.33 | 6.5 | N/A |

Based on the example parameters noted above, in accordance with one aspect of the technology, an optimal area or cross-section of the tube (taken generally perpendicular to a longitudinal axis of the tube) may be computed based on the desired flow rate. Typically, flow rates are determined based on oxygen saturation level prescribed by medical personnel. In one aspect of the technology, a desired flow rate is divided by six to obtain an optimal cross-sectional area. The inside diameter of the tube is then derived from mathematical computation.

In one aspect of the technology, to achieve the greatest distance of separation of the delivery tube from the patient's face while still maintaining optimal oxygen stream collimation, an exit velocity of oxygen is approximately one meter per second (or one hundred centimeters/sec). To achieve that exit velocity with an optimal collimation distance, the diameter of tube 10 is calculated as follows: LPM is first converted to cubic centimeters per second; With 100 cm/second being equal to the target exit velocity the tube inside diameter D is calculated as D=2*√(LPM*5.3). In a situation involving a two-tube delivery system, as described above, the inside tube diameter is computed by using one half the LPM for each tube. In one aspect of the technology involving a two-tube system, the target exit velocity for the two-tube delivery system is still approximately one meter per second.

It is understood and contemplated herein that greater than two-tube systems could be used herein. For example, a three-tube system may be used with distal ends of tubes arranged about the patient to optimize the oxygen "envelope" about the face of the patient. As with the other aspects described herein, the exit velocity from the distal end of the tubing is approximately one meter per second. The inside diameter of the tubing is calculated using the preferred velocity of one meter per second and one third the LPM for each tube.

Figure 8:
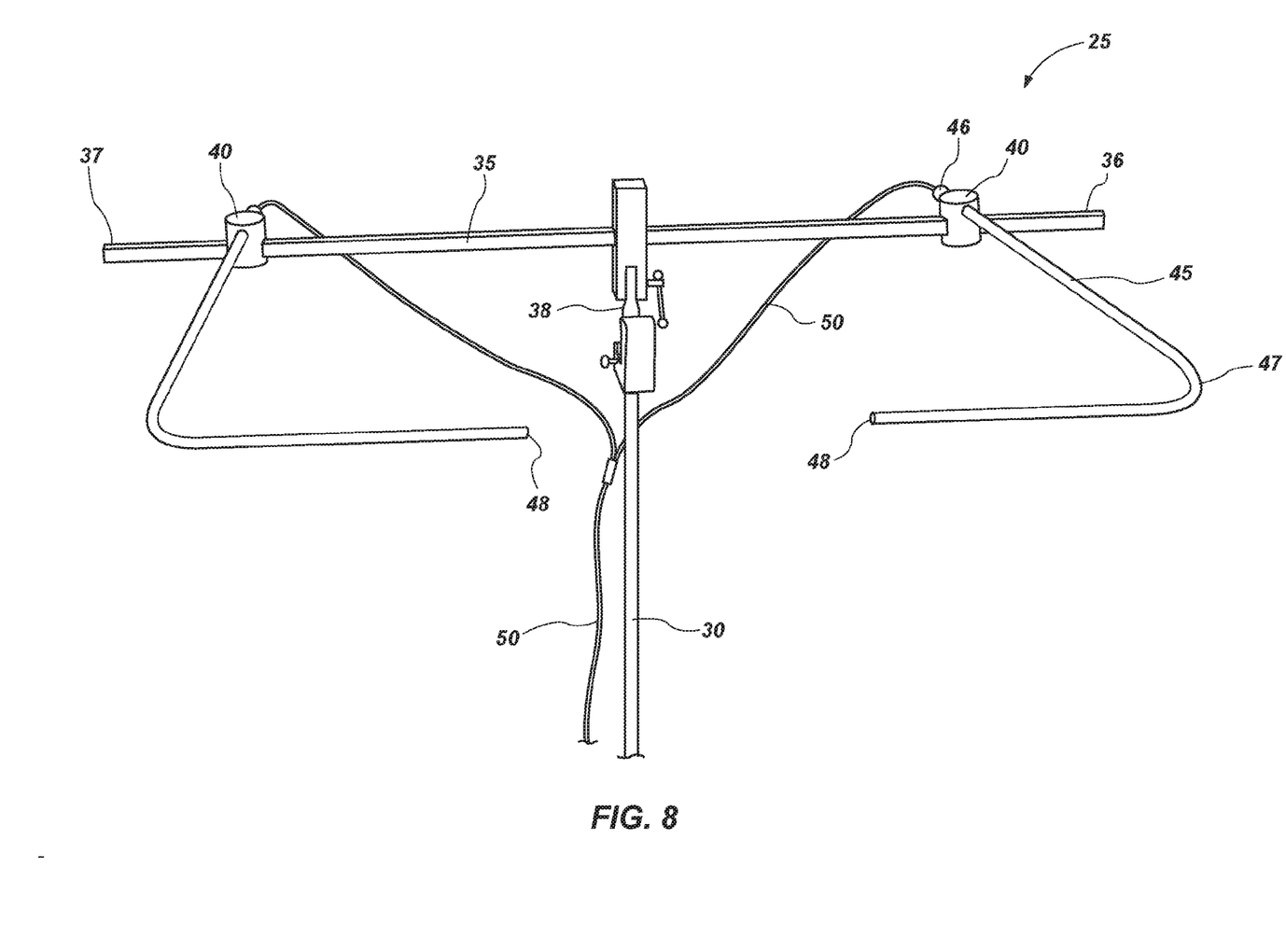
FIG. 8 is an oxygen delivery system in accordance with one aspect of the technology.

With reference now to FIG. 8, an oxygen delivery system 25 is shown in accordance with one aspect of the technology. The system 25 comprises a vertical stand 30 and a horizontal crossbar 35 mounted perpendicular to the stand 30. The crossbar 35 extends laterally away from the stand 30. An attachment device 40 is disposed on opposing distal ends 36, 37 of the crossbar 35. The attachment device 40 comprises a first aperture for receiving the crossbar 35 there through and a second aperture for receiving a rigid elongate tubular member 45 there through. A proximal end 46 of the rigid elongate tubular member 45 is coupled to flexible tubing 50 which is operatively coupled to a pump and source of oxygen. The rigid elongate tubular member 45 extends laterally outward and perpendicular to the crossbar 35. The elongate tubular member 45 has a ninety degree bend 47 with a distal end 48. In one aspect of the technology, the bend 47 in the elongate tubular member 45 is adjustable such that it may be changed to suit a particular position about the face of the patient. For example, in one aspect the bend 47 ranges from between forty-five and one hundred thirty-five degrees relative to the proximal end 46.

The attachment device 40 comprises a set screw adapted to frictionally engage a sidewall of the rigid elongate tubular members 45. In this manner, the relative position of the elongate rigid member 45 within the second aperture may be adjusted thereby adjusting the angle of the distal end 48 of the elongate rigid member 45 relative to the face of a stationary patient. The attachment device 40 may be moved laterally about the crossbar 35 to adjust the distance between the face of a stationary patient and the distal end 48 of the elongate rigid member 45. In one aspect of the technology, the crossbar 35 is coupled to the stand 30 by way of an adjustable pivot mechanism 38 to permit additional means to position the oxygen delivery system 25.

In another aspect of the technology, the rigid elongate tubular members 45 do not couple to a stand 30 and cross bar 35 assembly. Rather, the rigid elongate tubular members 45 couple to the sides or top of a patient's bed rail. In another aspect, the rigid elongate tubular members 45 couple to arm rests or other components of a chair, bed, or other area where the patient may remain stationary for a period of time. In this aspect, the rigid elongate tubular members 45 couples to the bed rail (or other element) by way of a clamp. It is understood, however, that any number of coupling means are contemplated for use to attach the rigid elongate tubular members 45 to the bed rail as suits a particular purpose.

The foregoing detailed description describes the technology with reference to specific exemplary aspects. However, it will be appreciated that various modifications and changes can be made without departing from the scope of the present technology as set forth in the appended claims. The detailed description and accompanying drawings are to be regarded as merely illustrative, rather than as restrictive, and all such modifications or changes, if any, are intended to fall within the scope of the present technology as described and set forth herein.

More specifically, while illustrative exemplary aspects of the technology have been described herein, the present technology is not limited to these aspects, but includes any and all aspects having modifications, omissions, combinations (e.g., of aspects across various aspects), adaptations and/or alterations as would be appreciated by those skilled in the art based on the foregoing detailed description. The limitations in the claims are to be interpreted broadly based on the language employed in the claims and not limited to examples described in the foregoing detailed description or during the prosecution of the application, which examples are to be construed as non-exclusive. For example, in the present disclosure, the term "preferably" is non-exclusive where it is intended to mean "preferably, but not limited to." Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus-function are expressly recited in the description herein. Accordingly, the scope of the technology should be determined solely by the appended claims and their legal equivalents, rather than by the descriptions and examples given above.

The invention claimed is:

1. A system for delivering oxygen to a substantially stationary target, comprising:
 a source of oxygen coupled to a delivery system, the delivery system comprising:
 at least two elongate hollow members each comprising a proximal end operatively coupled to the source of oxygen, and a substantially straight portion of tubing terminating in a distal end, and
 a target area disposed at least 150 mm in a clear path from the distal end of each of each of the elongate hollow members,
 wherein the substantially straight portion of the elongate hollow member is at least 300 mm in length, is longitudinally directed toward the target area and collimates a stream of oxygen such that the stream of oxygen exits the distal end of the elongate hollow members in a substantially collimated laminar state and transforms to a turbulent state when it reaches the target area; wherein the at least two elongate hollow members are disposed on opposite sides of the target oriented in opposing directions and the oxygen flow rate from the elongate hollow members is substantially equal.

2. The system of claim 1, wherein an angle of the elongate hollow member with respect to the target ranges between 10 and 45 degrees with respect to an imaginary plane that contains the centroid and the uppermost point of the target.

3. The system of claim 1, wherein the distal end of the elongate hollow member is configured to be disposed at least 150 mm and no greater than 300 mm from the target.

4. The system of claim 1, wherein an inner diameter of the elongate hollow member is between 5 mm and 16 mm.

5. The system of claim 1, wherein the flow rate of the stream of oxygen is between 2 and 10 liters per minute.

6. The system of claim 2, wherein the angle is 15 degrees.

7. A system for delivering oxygen to a target, comprising:
a pump configured to deliver oxygen to the target;
first and second elongate hollow members operatively coupled to the pump, the elongate hollow members configured to be positioned about the target such that a distal end of the elongate hollow members are in opposing directions and are disposed at least 150 mm in a clear path from the target, and wherein a substantially straight portion of tubing of each elongate hollow member having a low coefficient of friction is longitudinally directed toward the target, said substantially straight portion being at least 300 mm in length;
a first attachment device coupled to the first elongate hollow member and configured to position the first elongate hollow member, wherein the first attachment device is not in contact with the target;
a second attachment device coupled to the second elongate hollow member and configured to position the second elongate hollow member, wherein the second attachment device is not in contact with the target; and
a flow of oxygen delivered by the pump, emanating as a first stream of oxygen from the distal end of the first elongate hollow member and a second stream of oxygen from the distal end of the second elongate hollow member in a substantially collimated laminar state and extending from the elongate hollow members until the first and second streams of oxygen contact the target at which point the first and second streams of oxygen transform into a turbulent state.

8. The system of claim 7, wherein the first and second attachment devices are configured for attachment to a side rail of a bed of a patient.

9. The system of claim 7, wherein the first and second attachment devices are configured for attachment to a stationary stand positioned about a bed or chair of a patient.

10. The system of claim 7, further comprising an upright stand coupled to a horizontal cross bar, wherein the first and second attachment devices are coupled to opposing sides of the horizontal cross bar.

11. The system of claim 10, wherein the first elongate hollow member comprises a first portion extending outward from the first attachment device and a second portion disposed at an angle ranging from 45 to 135 degrees relative to the first portion, the second portion configured to extend toward the target, and wherein the second elongate hollow member comprises a first portion extending outward from the second attachment device and a second portion disposed at an angle ranging from 45 to 135 degrees relative to the first portion, the second portion configured to extend toward the target.

12. The system of claim 11, wherein the elongate hollow members are rotatable within the first and second attachment devices.

13. A method of delivering oxygen, comprising:
positioning a first elongate hollow member with a substantially straight portion of tubing longitudinally directed toward a target, wherein the substantially straight portion is at least 300 mm in length, and wherein a distal end of the elongate hollow member is positioned at least 150 mm in a clear path from the target;
transmitting a stream of oxygen through the first elongate hollow member at between approximately 2 and 10 liters per minute;
positioning the first elongate hollow member and a second elongate hollow member normal to the target, wherein the flow rate of oxygen through each of the two elongate hollow members is substantially equal and the direction of flow from the first and second elongate hollow members intersect with one another;
wherein the stream of oxygen exits the distal end of the elongate hollow member in a substantially collimated laminar state.

14. The method of claim 13, wherein an inner diameter of the elongate hollow member is between 5 mm and 16 mm.

15. The method of claim 13, wherein an exit velocity of the stream of oxygen from the elongate hollow member is one meter per second.

16. The method of claim 13, wherein an angle of the direction of oxygen flow is between 10 and 45 degrees with respect to an imaginary plane that contains the centroid and the uppermost point of the target.

17. The method of claim 13, further comprising an attachment device configured to couple the first elongate hollow member to an upright stand disposed about a patient.

* * * * *